United States Patent [19]

Nishimura et al.

[11] Patent Number: 4,598,095

[45] Date of Patent: Jul. 1, 1986

[54] ANTIVIRAL ISOTHIOSEMICARBAZONES

[76] Inventors: Tamio Nishimura, No. 5-4-11, Masukata, Tama-ku, Kawasaki-shi, Kanagawa; Hiroshige Toku, No. 16-5, Narusedai 3-chome, Machida-shi, Tokyo; Shin Yoshii, No. 14-27, Moegino, Midori-ku, Yokohama-shi, Kanagawa; Harumi Fukuyasu, No. 4-1-104, Maborikaigan, Yokosuka-shi, Kanagawa; Kuniomi Matsumoto, No. 2712-80, Naruse, Machida-shi, Tokyo; Youzo Kazuno, No. 1312-135, Uchikoshi-cho, Hachioji-shi, Tokyo; Tetsuro Watanabe, No. 390-3, Matsumi-cho 2-chome, Kanagawa-ku, Yokohama-shi, Kanagawa, all of Japan

[21] Appl. No.: 472,407

[22] Filed: Mar. 4, 1983

[30] Foreign Application Priority Data

Mar. 5, 1982 [JP] Japan .................................. 57-34062

[51] Int. Cl.[4] .................... A61K 31/155; A01N 37/52
[52] U.S. Cl. .................................................... 514/632
[58] Field of Search ....................... 260/453.4; 424/323

[56] References Cited

PUBLICATIONS

Asahi, "Polarography of Thioacetazone and its Related Compounds", Chem. Pharm. Bull. Japan, 11:930–938 (1963).
Toku et al, "Synthesis and Antimicrobial Activities of Isothiosemicarbazones", J. Antibact. Antifung. Agents, 9(12): 551–561 (1981), Bokin Bobai.
Chem. Abstracts, vol. 96: 162266a (1982).
Index Chemicus II, No. 33019 (1963).
Nishimura et al, "Antiviral Compounds, VII, Synthesis and Anti-influenza VVirus Activity of Alkoxyacetophenone Amidinohydrazones", Kitasato Arch. of Exp. Med. 48: 125–130 (1975).
Nishimura et al, "Antiviral Compounds, VI, Synthesis and Anti-influenza Virus Activity of Alkoxybenzyalacetone Amidinohydrazones", Kitasato Arch. of Exp. Med. 48: 23–30 (1975).
Nishimura et al, "Antiviral Compounds, IX, Synthesis and Anti-influenza Virus Activity of Bis-Amidinohydrazones of Glyoxal and Methylglyoxal, " Kitasato Arch. of Exp. Med. 48(4): 171–181 (1975).
Hirai et al, "Effect of Thiosemicarbazones on the Multiplication of Tobacco Mosaic Virus", Nature 181: 352–353 (1958).
Nishimura et al, "Antibacterial Activities of Amidinohydrazones of Benzalacetones, Cinnamaldehydes, Acetophenones and Benzaldehydes", Kitasato Arch. of Exp. Med., 46: 43–81 (1973).
Nishimura et al, "Antiviral Compounds, XII, Antiviral Activity of Amidinohydrazones of Alkoxyphenyl-substituted Carbonyl Compounds Against Influenza Virus in Eggs and in Mice", Kitasato Arch. of Exp. Med., 50: 39–46 (1977).
Nishimura et al, "Antiviral Compounds, VIII, Synthesis and Anti-influenza Virus Activity of Amidinohydrazones of Alkoxybenzaldehydes and Alkoxycinnamaldehydes", Kitasato Arch. of Exp. Med., 48(4): 165–170 (1975).

Primary Examiner—Jerome D. Goldberg
Attorney, Agent, or Firm—Sughrue, Mion, Zinn, Macpeak & Seas

[57] ABSTRACT

An antiviral drug contains as its effective component an isothiosemicarbazone represented by the following general formula (I) or an acidic salt thereof:

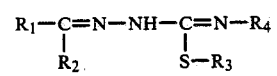

(I)

wherein $R_1$ represents a halogen atom, a lower ($C_1$–$C_6$) alkyl group, a hydroxy group, a phenyl group which may be or may not be substituted with an alkoxy group containing 1 to 12 carbon atoms, or an unsubstituted or substituted phenylethynyl group represented by the following general formula (II):

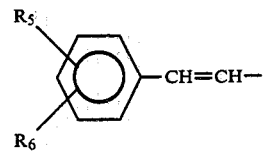

(II)

(wherein $R_5$ and $R_6$ may be the same or different, and they each represent a hydrogen atom, a halogen atom, a lower ($C_1$–$C_6$) alkyl group, a hydroxy group or an alkoxy group containing 1 to 12 carbon atoms); $R_2$ represents a hydrogen atom or a lower ($C_1$–$C_6$) alkyl group; $R_3$ represents a lower ($C_1$–$C_6$) alkyl group or a benzyl group; $R_4$ represents a hydrogen atom or a lower ($C_1$–$C_6$) alkyl group. Many of these effective component compounds not only have antiviral activity (especially against influenza virus), but also prevent the breeding of and exterminate plant pathogenic molds.

5 Claims, No Drawings

ANTIVIRAL ISOTHIOSEMICARBAZONES

BACKGROUND OF THE INVENTION

Methods for preparing isothiosemicarbazones have been disclosed in *Bokin Bobai,* Vol. 9, No. 12, pp. 551-561 (1981). Furthermore, *Bokin Bobai* discloses that certain of the compounds useful as antiviral compounds in the present invention have weak antibacterial activity. In addition, certain thiosemicarbazones or amidinohydrazone compounds have heretofore been known to have an antiviral activity, as described in *Kitasato Arch. of Exp. Med.,* Vol. 46, pp. 73-81 (1973); ibid., Vol. 48, pp. 23-30 (1975); ibid., Vol. 48, pp. 125-130 (1975); ibid., Vol. 48, pp. 165-170 (1975); ibid., Vol. 48, pp. 171-181 (1975); ibid., Vol. 50, pp. 39-46 (1977); and *Nature,* Vol. 181, pp. 352-353 (1958).

SUMMARY OF THE INVENTION

An object of the present invention is to provide antiviral compositions.

Another object of the present invention is to provide compositions capable of inhibiting viral proliferation and/or capable of acting as a virusicide.

A further object of the present invention is to provide methods for killing infectious viruses such as influenza and/or inhibiting their proliferation.

A further object of the present invention is to provide compositions capable of preventing the breeding of and capable of exterminating plant pathogenic fungi.

Another object of the present invention is to provide methods for eradicating and/or preventing infection by plant pathogenic fungi.

Other objects of this invention will be apparent from the Detailed Description of the Invention, hereinafter.

In accordance with one embodiment of the present invention, there is provided a novel antiviral composition. More specifically, the present invention relates to an antiviral composition such as a drug which contains as its antivirally active component an isothiosemicarbazone represented by the following general formula (I) or an acidic salt thereof:

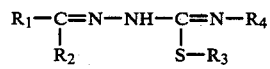

(I)

wherein $R_1$ represents a halogen atom, a lower alkyl group, a hydroxy group, a phenyl group which may be or may not be substituted with an alkoxy group containing 1 to 12 carbon atoms, or a substituted or non-substituted phenylethynyl group represented by the following general formula (II):

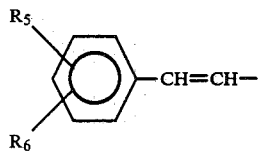

(II)

(wherein $R_5$ and $R_6$ may be the same or different, and they each represent a hydrogen atom, a halogen atom, a lower alkyl group, a hydroxy group or an alkoxy group containing 1 to 12 carbon atoms); $R_2$ represents a hydrogen atom or a lower alkyl group; $R_3$ represents a lower alkyl group or a benzyl group; and $R_4$ represents a hydrogen atom or a lower alkyl group, and the use of the compounds of the above formula (I) to kill and/or prevent the proliferation of viruses, particularly infectious viruses such as influenza virus.

Another aspect of the present invention provides antifungal compositions containing an antifungally effective amount of a compound of the above formula (I) capable of eradicating and/or preventing infection by pathogenic fungi, and the use of said antifungally effective compounds to prevent the breeding and infection caused by pathogenic fungi, particularly plant pathogenic fungi.

As used herein, lower alkyl group means an alkyl group containing 1 to 6 carbon atoms and halogen includes fluorine, chlorine, bromine and iodine.

DETAILED DESCRIPTION OF THE INVENTION isothiosemicarbazones of this invention, which are represented by the above-described general formula (I), are easily prepared with high yields by reacting an aldehyde or ketone represented by the general formula,

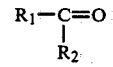

(wherein each of $R_1$ and $R_2$ have the same meaning as in the general formula (I), respectively), with a thiosemicarbazide represented by the general formula,

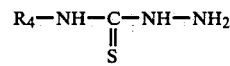

(wherein $R_4$ has the same meanings as in the general formula (I)), to provide a thiosemicarbazone represented by the general formula,

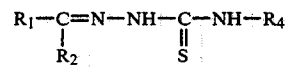

(wherein each of $R_1$, $R_2$ and $R_4$ have the same meaning as described above, respectively), and then by reacting the thus-produced thiosemicarbazone with a halide represented by the general formula, $X-R_3$ (wherein X represents a halogen atom, and $R_3$ has the same meaning as described above). Also, the isothiosemicarbazones may be prepared by reacting a carbonyl compound represented by the above-described formula,

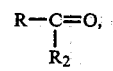

with an isothiosemicarbazide represented by the general formula,

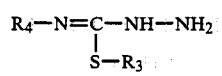

(wherein $R_3$ and $R_4$ have the same meanings as described above, respectively). These methods for preparing isothiosemicarbazones have been reported in the above-mentioned *Bokin Bobai* (translated as "Journal of Antibacterial and Antifungal Agents"), Vol. 9, No. 12, pp. 551–561 (1981).

Among the compounds to be used as the effective antiviral component of the compositions and methods of this invention, though many of them are known compounds, the compounds having compound numbers 6, 9, 11, to 16, 31, 32, 41, 45, 46 and 47, respectively, in Table 1 hereinafter are novel compounds which have not been described in the literature. The foregoing literature discloses that the known compounds have a weak antibacterial activity. On the other hand, it has not been known that isothiosemicarbazones have an antiviral activity. As a result of our examination of activities of isothiosemicarbazones against influenza virus using a hen's chorioallantoic membrane culture method, it has now been found that isothiosemicarbazones represented by the foregoing general formula (I) have a great proliferation-inhibiting activity and a considerable virucidal activity.

Specific examples of isothiosemicarbazones which can be employed as the antiviral component of the compositions and methods of this invention are set forth in the following Table 1, and are not intended to illustrate the scope of the present invention.

TABLE 1

$$\begin{array}{c} R_1 \\ \phantom{R_1}\diagdown \\ \phantom{R_1}\phantom{\diagdown}C=N-NH-C=N-R_4 \\ \phantom{R_1}\diagup \phantom{CNNHC}| \\ R_2 \phantom{CNNHCNR_4}S-R_3 \cdot HX \end{array}$$

| Compound No. | $R_1$ | $R_2$ | $R_3$ | $R_4$ | HX | Melting Point (°C.) |
|---|---|---|---|---|---|---|
| 1 |  | H | $CH_3$ | H | HCl | 169–171 |
| 2 |  | H | $-CH_2-$ | H | HCl | 189–190 |
| 3 | 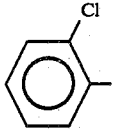 | H | $CH_3$ | H | HCl | 168 |
| 4 | 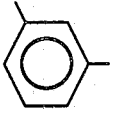 | H | $CH_3$ | H | HCl | 182 |
| 5 | 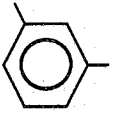 | H | $CH_3$ | $CH_3$ | HCl | 191 |
| 6 | 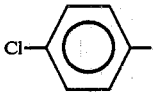 | H | $CH_3$ | H | HCl | 200–201 |
| 7 |  | H | $CH_3$ | $CH_3$ | HCl | 192–193 |
| 8 | 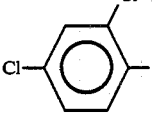 | H | $CH_3$ | H | HCl | 199–200 |

TABLE 1-continued
$$\begin{array}{c}R_1\\ \phantom{R_2}\diagdown\\ \phantom{R_2}C=N-NH-C=N-R_4\\ R_2\diagup\phantom{C=N-NH-}|\phantom{=N-R_4}\\ \phantom{R_2\diagup C=N-NH-}S-R_3\cdot HX\end{array}$$
| Compound No. | $R_1$ | $R_2$ | $R_3$ | $R_4$ | HX | Melting Point (°C.) |
|---|---|---|---|---|---|---|
| 9 | 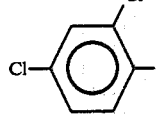 2,4-Cl | H | $C_4H_9$ | H | HCl | 203–205 |
| 10 | 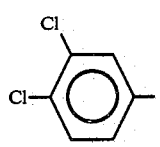 3,4-Cl | H | $CH_3$ | $CH_3$ | — | 92–95 |
| 11 | 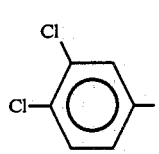 3,4-Cl | H | $CH_3$ | H | HCl | 217–218 |
| 12 | 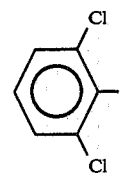 2,6-Cl | H | $CH_3$ | H | HCl | 182–183 |
| 13 | 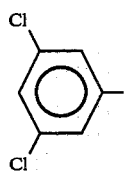 3,5-Cl | H | $CH_3$ | H | HCl | 201–202 |
| 14 | 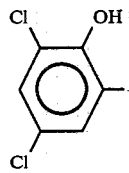 Cl, OH, Cl | H | $CH_3$ | H | HCl | 227–228 |
| 15 | 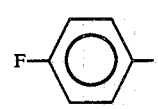 F | H | $C_4H_9$ | H | HCl | 188–190 |
| 16 | 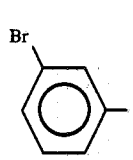 Br | H | $CH_3$ | H | HCl | 192–193 |
| 17 | 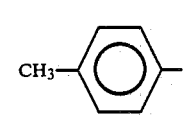 $CH_3$ | H | $CH_3$ | H | HCl | 175–176 |
| 18 | 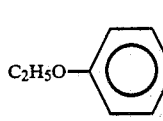 $C_2H_5O$ | H | $CH_3$ | H | — | 90–92 |

TABLE 1-continued $$\begin{matrix} R_1 \\ \phantom{R}\diagdown \\ \phantom{RR}C=N-NH-C=N-R_4 \\ \diagup \phantom{RRRRRRRR} | \\ R_2 \phantom{RRRRRR} S-R_3 \cdot HX \end{matrix}$$

| Compound No. | $R_1$ | $R_2$ | $R_3$ | $R_4$ | HX | Melting Point (°C.) |
|---|---|---|---|---|---|---|
| 19 | 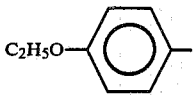 C$_2$H$_5$O— | H | C$_4$H$_9$ | H | HCl | 155–157 |
| 20 | 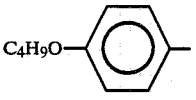 C$_4$H$_9$O— | H | CH$_3$ | H | — | 96–97 |
| 21 | 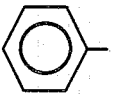 | CH$_3$ | CH$_3$ | H | HCl | 203–204 |
| 22 | 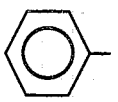 | CH$_3$ | —CH$_2$—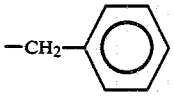 | H | HCl | 211–212 |
| 23 | 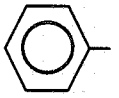 | C$_3$H$_7$ | CH$_3$ | H | HCl | 191–192 |
| 24 | 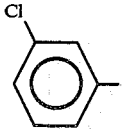 Cl— (ortho) | CH$_3$ | CH$_3$ | H | HCl | 223 |
| 25 |  Cl— | CH$_3$ | CH$_3$ | H | HCl | 222 |
| 26 | 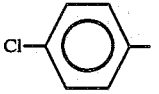 Cl— | C$_2$H$_5$ | CH$_3$ | H | HCl | 188–189 |
| 27 |  Cl— | C$_3$H$_7$ | CH$_3$ | H | HCl | 206–207 |
| 28 |  Cl— | C$_3$H$_7$ | CH$_3$ | CH$_3$ | HI | 180–181 |
| 29 | 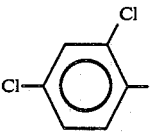 Cl, Cl— (2,4-di) | CH$_3$ | CH$_3$ | H | HCl | 168 |

TABLE 1-continued $$R_1\!\!>\!\!C\!\!=\!\!N\!\!-\!\!NH\!\!-\!\!\underset{S-R_3.HX}{\overset{|}{C}}\!\!=\!\!N\!\!-\!\!R_4$$

| Compound No. | $R_1$ | $R_2$ | $R_3$ | $R_4$ | HX | Melting Point (°C.) |
|---|---|---|---|---|---|---|
| 30 | 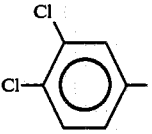 3,4-diCl-C₆H₃– | $CH_3$ | $CH_3$ | H | HCl | 229 |
| 31 | 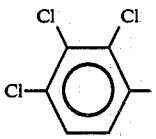 2,3,4-triCl-C₆H₂– | $CH_3$ | $CH_3$ | H | HCl | 202–204 |
| 32 | 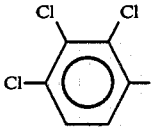 2,3,4-triCl-C₆H₂– | $CH_3$ | $C_4H_9$ | H | HCl | 176–178 |
| 33 | 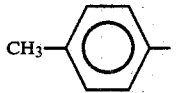 4-CH₃-C₆H₄– | $CH_3$ | $CH_3$ | H | HCl | 222 |
| 34 | 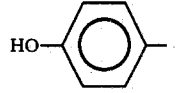 4-HO-C₆H₄– | $CH_3$ | $CH_3$ | H | HCl | 211–212 |
| 35 | 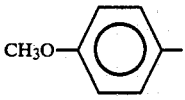 4-CH₃O-C₆H₄– | $CH_3$ | $CH_3$ | H | HCl | 200–201 |
| 36 | 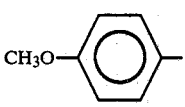 4-CH₃O-C₆H₄– | $CH_3$ | $C_4H_9$ | H | HCl | 155–156 |
| 37 | 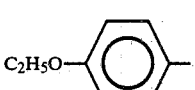 4-C₂H₅O-C₆H₄– | $CH_3$ | $CH_3$ | H | HCl | 214 |
| 38 | 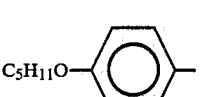 4-C₅H₁₁O-C₆H₄– | $CH_3$ | $CH_3$ | H | — | 86–87 |
| 39 | 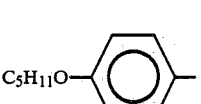 4-C₅H₁₁O-C₆H₄– | $CH_3$ | $C_4H_9$ | H | HCl | 178–180 |
| 40 |  4-C₈H₁₇O-C₆H₄– | $CH_3$ | $CH_3$ | H | — | 54–56 |

TABLE 1-continued $$R_1 \atop R_2 \!\!\!\diagup\!\!\!\! C\!=\!N\!-\!NH\!-\!\underset{S-R_3.HX}{C}\!=\!N\!-\!R_4$$

| Compound No. | $R_1$ | $R_2$ | $R_3$ | $R_4$ | HX | Melting Point (°C.) |
|---|---|---|---|---|---|---|
| 41 | $C_{10}H_{21}O\text{-}C_6H_4\text{-}$ | $CH_3$ | $CH_3$ | H | HCl | 179–181 |
| 42 | $Cl\text{-}C_6H_4\text{-}CH\!=\!CH\text{-}$ | $CH_3$ | $CH_3$ | H | — | 129–131 |
| 43 | $C_2H_5O\text{-}C_6H_4\text{-}CH\!=\!CH\text{-}$ | $CH_3$ | $CH_3$ | H | — | 99–101 |
| 44 | $C_4H_9O\text{-}C_6H_4\text{-}CH\!=\!CH\text{-}$ | $CH_3$ | $CH_3$ | H | — | 115–117 |
| 45 | $C_6H_{13}O\text{-}C_6H_4\text{-}CH\!=\!CH\text{-}$ | $CH_3$ | $CH_3$ | H | HCl | 182–183 |
| 46 | $C_{12}H_{25}O\text{-}C_6H_4\text{-}CH\!=\!CH\text{-}$ | $CH_3$ | $CH_3$ | H | HCl | 162–163 |
| 47 | $CH_3O,C_8H_{17}O\text{-}C_6H_3\text{-}CH\!=\!CH\text{-}$ | $CH_3$ | $CH_3$ | H | HCl | 169–170 |

Synthesis examples of the compounds used in this invention and examples examining their antiviral effect are set forth hereinafter. The antiviral compound of this invention can be expected to have an antiviral effect superior to that of the known antiviral adamantaneamine hydrochloride compounds.

In evaluating acute toxicity ($LD_{50}$ value) of the compounds of this invention, compound number 4 and compound number 25 of Table 1, respectively, were selected and examined for their acute toxicities by intraperitoneal administration to mice. The $LD_{50}$ values of compounds 4 and 25 have been found to be 200 mg/kg and 150 mg/kg, respectively. These values suggest that the antiviral compounds of this invention can be used in safety.

The antiviral drug of this invention can be prepared in various drug forms, e.g., in the form of a drug for oral administration, in a form for administration by injection, etc., using conventional pharmaceutical manufacturing techniques. However, it is more suitable for the antiviral drug of this invention to be used in the form of an oral drug.

A dosage of a drug for an individual depends on degree of seriousness of disease, weight and other conditions. As a suggested antiviral dosage for the compounds of this invention, from 10 to 100 mg/person can be administered once a day or in several installments a day.

This invention will now be illustrated in more detail by reference to the following synthesis examples and utility examination examples. In addition to their antiviral activity, the antiviral compounds of this invention also have been found through in vivo experimentation to exhibit an excellent effect in controlling against plant pathogenic fungus, e.g., rice blast, etc. Utility examination examples of this pesticidal, i.e., fungicidal effect, are also set forth below. The compounds of the formula (I) can be used to prepare various liquid, powder, wettable powder and the like compositions for external application to plants. Other conventional carriers, surface active agents and the like can be employed by the skilled artisan in preparing antifungal compositions. In addition, the Examples hereinbelow illustrate antifungal dosage ranges.

Firstly, several synthesis examples of isothiosemicarbazones and their acidic salts which are to be employed in this invention are described. The compound No. corresponds to the number in Table 1.

SYNTHESIS EXAMPLE 1

Synthesis of 4'-Chlorobenzaldehyde-S-methylisothiosemicarbazone Hydrochloride (Compound No. 6)

To a solution of 1.41 g (0.01 mole) of 4-chlorobenzaldehyde and 1.41 g (0.01 mole) of S-methylisothiosemicarbazide hydrochloride in 7 ml of methanol, hydrochloric acid was added in order to render the solution acidic. The resulting solution was refluxed for 30 minutes. Then, it was filtered while hot. The filtrate was cooled by allowing it to stand in contact with air and therefrom colorless needles separated out. The crystals were filtered off and had a melting point of 200°–201.5° C. Yield was 1.75 g. The same substance was additionally obtained in an amount of 0.21 g by recrystallizing from the resulting filtrate using diethyl ether. Therefore, the total yield was 1.96 g (74%).

Compounds having compound numbers 1, 3, 4, 8, 12, 13, 14, 16, 17, 21, 23, 24, 25, 26, 27, 29, 30, 33, 34, 35 and 37, respectively, were synthesized in the same manner as described above except that the corresponding carbonyl compounds were employed instead of 4-chlorobenzaldehyde.

SYNTHESIS EXAMPLE 2

Synthesis of 2',4'-Dichlorobenzaldehyde-S-butylisothiosemicarbazone Hydrochloride (Compound No. 9)

To a solution of 1.90 g (0.01 mole) of 2,4-dichlorobenzaldehyde and 2.75 g (0.01 mole) of S-butylisothiosemicarbazide hydroiodide in 25 ml of 85% ethanol, hydrochloric acid was added to render the solution acidic. The resulting solution was refluxed for 30 minutes. After cooling, a precipitate separated out, and was filtered off to obtain 2.9 g of solid. The solid was dissolved in dilute hot ethanol and then a water solution containing 1.7 g of lead acetate trihydrate was added thereto. Thereupon, a precipitate was deposited. The precipitate was filtered out, and the filtrate was rendered acidic with hydrochloric acid and then concentrated until crystals separated out. The crystals were filtered off, and recrystallized from 65% ethanol. Thus, colorless grains having a melting point of 203°–205° C. were obtained with a yield of 1.6 g (54%).

Compounds corresponding to compound numbers 15, 19, 32, 36 and 39, respectively, were synthesized in the same manner as described in Synthesis Example 2 except that the corresponding carbonyl compounds were used in place of 2,4-dichlorobenzaldehyde.

SYNTHESIS EXAMPLE 3

Synthesis of 3',4'-Dichlorobenzaldehyde-S-methylisothiosemicarbazone Hydrochloride (Compound No. 11)

To a solution of 2.6 g (0.15 mole) of 3,4-dichlorobenzaldehyde and 3.5 g (0.15 mole) of S-methylisothiosemicarbazole hydroiodide in 25 ml of 85% ethanol, hydrochloric acid was added to render the solution acidic. The resulting solution was refluxed for 30 minutes. After cooling, crystals separated out, and they were filtered off. A 4.2 g portion of the thus-obtained crystals was dissolved in dilute hot ethanol, and a water solution containing 1.6 g of lead acetate trihydrate was added thereto to deposit a precipitate. The precipitate was filtered out, and the filtrate was concentrated and then it was rendered acidic using hydrochloric acid. Thereupon, crystals separated out, and they were filtered off, and recrystallized from ethanol. Thus, 1.9 g (yield: 74%) of colorless needles having a melting point of 217°–218° C. was obtained. The corresponding free base can be extracted from the concentrated filtrate with diethyl ether.

Compounds corresponding to compound numbers 18, 20, 31, 38, 40, 41, 42, 43, 44, 45, 46 and 47, respectively, were synthesized in the same manner as described in Synthesis Example 3 except that the corresponding carbonyl compounds were used in place of dichlorobenzaldehyde.

SYNTHESIS EXAMPLE 4

Synthesis of Benzaldehyde-S-benzylisothiosemicarbazone Hydrochloride (Compound No. 2)

To a solution of 1.79 g (0.01 mole) of benzaldehyde-thiosemicarbazone in 10 ml of methanol, 1.27 g (0.01 mole) of benzyl chloride was added under reflux, and the refluxing was continued for 20 minutes. After cooling, crystals deposited and were filtered off, dissolved in methanol and then diethyl ether was added thereto (for recrystallization). Thereupon, colorless needles separated out. Melting point: 180°–190° C. Yield: 2.44 g (80%).

The compound having compound number 22 was obtained in the same manner as described above except that acetophenonethiosemicarbazone was used in place of benzaldehydethiosemicarbazone.

SYNTHESIS EXAMPLE 5

Synthesis of 3'-Chlorobenzaldehyde-S-methyl-4-N-methylisothiosemicarbazone Hydrochloride (Compound No. 5)

A solution of 2.47 g (0.01 mole) of S-methyl-4-N-methylisothiosemicarbazide hydroiodide and 1.40 g (0.01 mole) of 3-chlorobenzaldehyde in 15 ml of methanol was rendered acidic using hydrochloric acid, and refluxed for 30 minutes. After cooling, diethyl ether was added to the solution and thereby a precipitate was deposited. The precipitate was filtered off, dissolved again in a small amount of ethanol, and neutralized with a sodium hydroxide solution. The thus-produced free base was extracted with diethyl ether, dried with sodium sulfate anhydride and then hydrogen chloride was bubbled therethrough. Thereupon, colorless needles separated out. Melting point: 191° C. Yield: 1.80 g (65%).

Compounds No. 7, No. 10 and No. 28 were synthesized in the same manner as described above using the corresponding carbonyl compounds, and obtained in the form of the hydrochloride, the free base and the hydroiodide, respectively.

All of the thus-synthesized compounds were identified by elemental analysis and infrared spectra.

The antiviral effect of the compounds of this invention will now be illustrated by the following examination examples.

EXAMINATION EXAMPLE 1

Examination of Virucidal Activity and Virus Proliferation-Inhibiting Activity Using Hen's Egg Chorioallantoic Membrane Culture Method The following tests (1) to (3) were employed for examining the antiviral activity using the known method as described in T. Nishimura et al., *International Congress of Chemotherapy* in 1971, pp. 325–327.

(1) Toxicity Test to Hen's Egg Chorioallantoic Membrane

A piece of circular chorioallantoic membrane having a diameter of 30 mm was added into a 0.9 ml of a Hanks' balanced salt solution (BSS) placed in a chorioallantoic membrane culture tube. A number of such tubes were prepared. Into each tube, one of the solutions of the compound of this invention prepared by serial two-fold dilution was added in an amount of 0.1 ml, and shake culture was carried out at 36° C. for 48 hours. After the incubation, the chorioallantoic membrane was washed with phosphate buffer solution (PBS), dipped in a Trypan Blue solution for 1 minute, and again thoroughly washed with PBS. The concentration at which two of four pieces of the chorioallantoic membranes employed for each diluting step of the drug were dyed in a dark blue color was defined as the 50% toxicity concentration.

(2) Virucidal Test in vitro

An equal volume (0.5 ml) of influenza virus, Adachi strain of $A_2$-type (1000 $MID_{100}$/ml) was admixed with each of 0.5 ml solutions of the compound of this invention prepared by serial ten-fold or two-fold dilution, and the resulting mixture was allowed to stand at room temperature for 120 minutes. Thereafter, it was diluted 100-fold. A 0.2 ml portion of the diluted mixture was added into a chorioallantoic membrane culture tube in which 0.8 ml of Hanks' solution BSS had been previously placed, and shake culture was carried out at 36° C. for 48 hours. After the incubation, the presence of hemagglutination was investigated during the hemagglutination test, and the 50% virucidal concentration was determined by the Reed and Muench method.

(3) Virus Proliferation-Inhibiting Test

Each of 0.1 ml portions of solutions of the compound of this invention prepared by serial 2-fold dilution was added into a chorioallantoic membrane culture tube in which a 0.8 ml portion of Hank's solution BSS had already been placed, and the chorioallantoic membrane was inoculated with a 0.1 ml portion of influenza virus, Adachi strain of $A_2$-type (100 $MID_{100}$/ml), and shake culture was carried out at 36° C. for 48 hours. After the incubation, the 50% virus proliferation-inhibiting concentration was determined in the same manner as described in the virucidal test in vitro.

(4) Determination of Virucidal Index and Virus Proliferation-Inhibiting Index

A virucidal index and a virus proliferation-inhibiting index were determined by dividing the 50% toxicity concentration of the compound to the chorioallantoic membrane by the 50% virucidal concentration and the 50% virus proliferation-inhibiting concentration, respectively.

Results of the above-described tests are set forth in the following Table 2.

TABLE 2

Antiviral Activity of Isothiosemicarbazones

| Compound No. | Toxicity Concentration to Chorioallantoic Membrane (mcg/ml) | 50% Virus Proliferation-Inhibiting Concentration (mcg/ml) [Index]* | 50% Virucidal Concentration (mcg/ml) [Index]** |
|---|---|---|---|
| 4 | >1,000 | 18.5 [>54.0] | 175 [5.7] |
| 8 | 706 | 19.8 [35.7] | 46.4 [15.2] |
| 9 | 632.5 | 115 [5.5] | 31.6 [19.9] |
| 11 | 707 | 21.3 [33.2] | 46.4 [15.2] |
| 13 | 700 | 50 [14.0] | — — |
| 14 | >1,000 | 15 [>66.7] | — — |
| 19 | >1,000 | 39.7 [>25.2] | 316 [3.2] |
| 21 | 157.5 | 12.5 [12.6] | — — |
| 24 | 707.5 | 25 [28.3] | 215 [3.3] |
| 25 | 354.2 | 14.4 [24.6] | 215 [1.7] |
| 28 | 793.8 | 63 [12.6] | — — |
| 29 | 180 | 23.2 [7.7] | 100 [1.8] |
| 31 | 353.6 | 21.3 [16.6] | — — |
| 33 | 1,000 | 50 [20.0] | — — |
| 35 | 99.4 | 14.2 [7.0] | — — |
| 37 | 88.8 | 12.5 [7.1] | — — |
| 38 | >1,000 | 126 [>8.0] | — — |
| 41 | 1,000 | >200 [<5.0] | 145 [6.9] |
| 42 | 710 | 100 [7.1] | 170 [4.2] |
| 43 | >1,000 | 141 [7.1] | 316 [3.2] |
| 46 | >1,000 | 85.2 [>11.7] | 31.6 [>31.6] |
| Am | 1,000 | 32.9 [30.4] | 648.8 [1.5] |

Am: Adamantaneamine Hydrochloride (Reference)
*Number in brackets represents virus proliferation-inhibiting index.
**Number in brackets represents virucidal index.

As can be seen from examination of the results in Table 2, the isothiosemicarbazones of this invention exhibited a strong virus proliferation-inhibiting activity and a lower toxicity to the chorioallantoic membrane than adamantaneamine hydrochloride employed as a control sample. That is, the present invention provides compounds having an excellent proliferation-inhibiting activity. In addition, in contrast to the absence of virucidal activity in the case of adamantaneamine hydrochloride, many of the isothiosemicarbazones of this invention were found to have a strong virucidal activity. Therefore, isothiosemicarbazones of this invention are safer to use and are expected to have a better antiviral effect, as compared with adamantaneamine hydrochloride employed as a control sample. Thus, the term "antiviral" as used herein is inclusive of virusicide activity and/or inhibition of viral proliferation.

EXAMINATION EXAMPLE 2

Test for Controlling Rice Blast

Onto each of 8 rice seedlings (variety: Jukkoku) raised up to the 4-leaf stage in a plastic pot having a diameter of 6.5 cm, a test chemical solution prepared by dissolving and diluting each compound set forth in Table 1 so as to have a prescribed concentration was sprayed using a spray gun in a quantity of 35 ml per 3 pots. After drying in room atmosphere, these seedlings were placed in a moist chamber maintained at 24° C., and inoculated by uniformly spraying a conidial suspension of rice blast fungus (Pyricularia oryzae). After they were kept overnight in the moist chamber, the pots were transferred into a greenhouse. Seven days after the inoculation, the number of lesion was surveyed and counted. A protective value of test chemical was determined by the following equation:

$$\text{Protective Value (\%)} = \left(1 - \frac{\text{Average number of lesion in a treated lot}}{\text{Average number of lesion in a non-treated lot}}\right) \times 100$$

Examination results are shown in the following Table 3.

TABLE 3

Control Effect against Rice Blast

| Compound No. | Concentration (ppm) | Protective Value (%) |
| --- | --- | --- |
| 1 | 400 | 90 |
| 2 | " | 85 |
| 3 | " | 96 |
| 4 | " | 100 |
| 5 | " | 93 |
| 6 | " | 100 |
| 7 | " | 75 |
| 8 | " | 97 |
| 9 | " | 100 |
| 10 | " | 88 |
| 11 | " | 98 |
| 12 | " | 100 |
| 13 | " | 100 |
| 14 | " | 98 |
| 15 | " | 93 |
| 16 | " | 100 |
| 17 | " | 100 |
| 18 | " | 100 |
| 19 | " | 100 |
| 20 | " | 99 |
| 21 | " | 100 |
| 22 | " | 90 |
| 23 | " | 93 |
| 24 | " | 89 |
| 25 | " | 100 |
| 26 | " | 100 |
| 27 | " | 100 |
| 28 | " | 94 |
| 29 | " | 90 |
| 30 | " | 88 |
| 31 | " | 89 |
| 32 | " | 96 |
| 33 | " | 97 |
| 34 | " | 93 |
| 35 | " | 100 |
| 36 | " | 95 |
| 37 | " | 89 |
| 38 | " | 100 |
| 39 | " | 100 |
| 40 | " | 85 |
| 41 | " | 94 |
| 42 | " | 88 |
| 43 | " | 100 |
| 44 | " | 100 |
| 45 | " | 96 |
| 46 | " | 77 |
| 47 | " | 96 |
| Reference* fungicide | 300 | 96 |
| No spraying | — | 0 |

*As the reference fungicide, a commercially available fungicide, Hinosan Emulsion 30 (produced by Nihon Tokushu Noyaku Seizo K.K., which contains 30% of O—ethyl-S,S—diphenyldithiophosphate) was used.

The results of Table 3 demonstrate that the compounds set forth in Table 1 are excellent in controlling rice blast. These effects could not be contemplated from study of the literature disclosed hereinbefore. The results of Examination Example 3 further support the conclusion that the excellent controlling effect against rice blast could not be suggested from the MIC values described in the foregoing literature.

EXAMINATION EXAMPLE 3

Test for Controlling Rice Blast in Case of Low Dosage

The compounds set forth in Table 1 were used in low spraying concentrations, and examined for their respective controlling effects against rice blast in the same manner as employed in Examination Example 2. Results obtained are shown in Table 4.

TABLE 4

Control Effect against Rice Blast in Case of Low Dosage

| Compound No. | Concentration (ppm) | Protective Value (%) | MIC Value (mcg/ml) in Literature** |
| --- | --- | --- | --- |
| 10 | 100 | 67 | 12.5 |
| 30 | " | 66 | 12.5 |
| 18 | " | 99 | — |
| 19 | " | 93 | — |
| 20 | " | 100 | — |
| 43 | " | 97 | — |
| Reference* fungicide | 300 | 94 | — |
| No spraying | — | 0 | — |

*The same reference fungicide as in Examination Example 2 was used.
**MIC values described in the column of "Pyricularia oryzae" of Bokin Bobai, Vol. 9, No. 12, pages 551 to 561 (1981) was cited.

As can be seen from the results in Table 4, the compounds having compound numbers 10 and 30, whose MIC values were determined to be 12.5 mcg/ml, had low protective values and, on the other hand, the compounds having compound numbers 18, 19, 20 and 43, which had never been observed to have effects of inhibiting proliferation of any of the pathogenic fungi described in the foregoing literature, exhibited a very excellent controlling effects.

EXAMINATION EXAMPLE 4

Test for Controlling Effect against Cucumber Gray Mold

Onto each of 3 young cucumber seedlings (variety: *Cucumis sativus* L. cultivar, Tokiwa Jibai) grown up to the 2-leaf stage in a porous pot having the size of No. 3, a test chemical solution prepared by dissolving and diluting each compound set forth in Table 1 so as to have a prescribed concentration was sprayed using a spray gun in a quantity of 40 ml per 3 pots. After drying in room atmosphere, these cucumber seedlings were inoculated with the pathogenic fungi of cucumber gray mold (*Botrytis cinerea*) by uniformly spraying a suspension of hyphal pieces (previously prepared by culturing of the pathogenic fungi of cucumber gray mold (*Botrytis cinerea*) for 5 days on potato sucrose agar medium, grinding the thus-proliferated mycelium by means of a homogenizer and then adding glucose in a concentration of 0.5% for the purpose of accelerating the attack of the disease). Thereafter, the plants were placed in a moist chamber maintained at 24° C., and were attacked by the disease. Five days after the inoculation, the degree of the attack of the disease was examined. Therein, the state that no attack of the disease was observed was expressed by the index of 0, the state that the seedlings were rotted and withered up was expressed by the index of 5, and the indices of 1, 2, 3 and 4 were given to the intermediate states between the above-described states depending on the progressive degree of the symptom. A control value was determined by the following equation:

$$\text{Control Value (\%)} = \left(1 - \frac{\text{Average disease index of treated seedling}}{\text{Average disease index of non-treated seedling}}\right) \times 100$$

Examination results are shown in the following Table 5.

TABLE 5

Test for Controlling Effect against Cucumber Gray Mold

| Compound No. | Concentration (ppm) | Control Value (%) |
|---|---|---|
| 30 | 400 | 0 |
| 10 | " | 0 |
| 20 | " | 56 |
| 38 | " | 90 |
| 43 | " | 87 |
| Reference fungicide* | 500 | 83 |
| No spraying — | 0 | |

*Commercially available fungicide, Euparen wettable powder (produced by Nihon Tokushu Noyaku Seizo K.K., containing 50% of N'—(dichlorofluoromethylthio)-N,N'—dimethyl-N'—phenylsulfamide).

The results shown in Table 5 show the same tendency as that of rice blast. Namely, the compounds having compound numbers 30 and 10 which demonstrated an MIC value of 12.5 mcg/ml had no controlling effect at all and, on the other hand, the compounds having compound numbers 38 and 43, which were inactive against all of the plant pathogenic fungi in vitro experiments, exhibited a strong controlling effect.

The results described above reveal that antifungal activity in vitro cannot be correlated to the controlling effect in vivo.

While the invention has been described in detail and with reference to specific embodiments thereof, it will be apparent to one skilled in the art that various changes and modifications can be made therein without departing from the spirit and scope thereof.

What is claimed is:

1. A process for treating a subject having an $A_2$-type influenza virus infection which comprises administering orally or by injection an anti $A_2$-type influenza viral effective amount of an isothiosemicarbazone represented by the following general formula (I) or an acidic salt thereof:

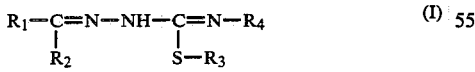

wherein $R_1$ represents an unsubstituted phenyl group or a phenyl group substituted by at least one of 1 to 3 halogen atoms selected from the group consisting of fluorine, chlorine and bromine, a methyl group substituted in the para position of the phenyl group, a hydroxyl group, or an alkoxy group containing 1 to 12 carbon atoms substituted in the para position of the phenyl group, or an unsubstituted or substituted phenylethynyl group represented by the following general formula (II)

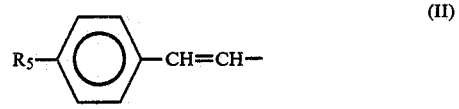

wherein $R_5$ represents a chlorine atom, or an alkoxy group containing 1 to 12 carbon atoms; $R_2$ represents a hydrogen atom or a $C_1-C_6$ alkyl group; and $R_3$ represents a $C_1-C_6$ alkyl group; and $R_4$ represents a hydrogen atom or a methyl group, to said subject.

2. The process of claim 1 wherein said phenyl group is substituted in the para-position.

3. The process of claim 2 wherein said phenyl group is substituted by a halogen atom in the para-position.

4. The process of claim 2 wherein said phenyl group is substituted by said alkoxy group in the para-position.

5. The process of claim 1 wherein said isothiosemicarbazone is selected from the group consisting of

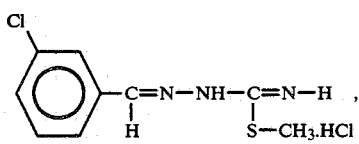

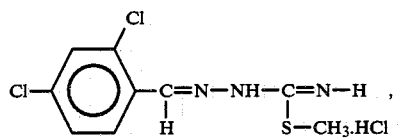

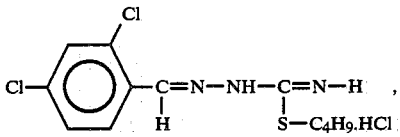

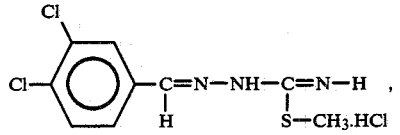

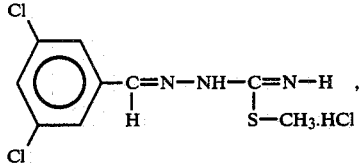

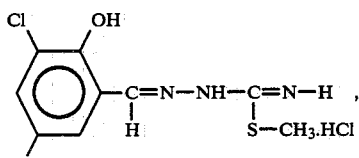

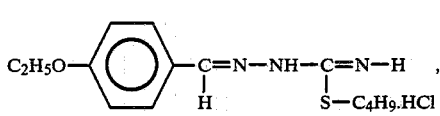

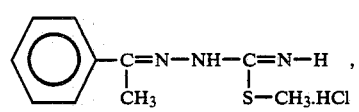

-continued
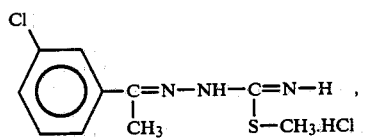
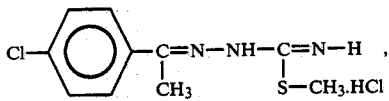
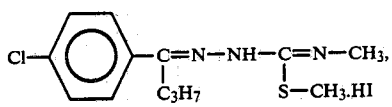
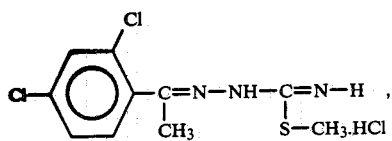
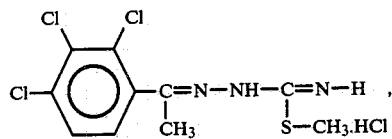
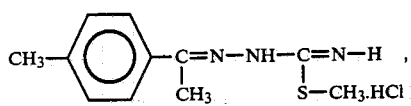
-continued
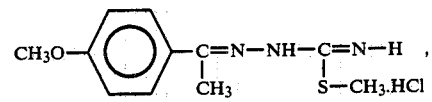
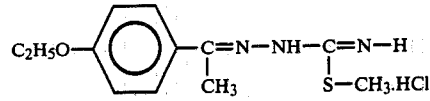
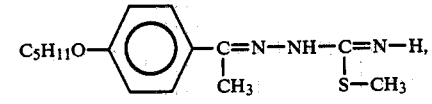
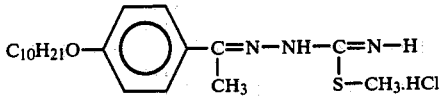
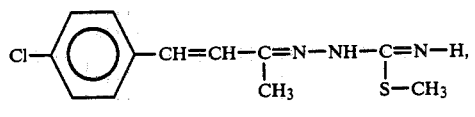
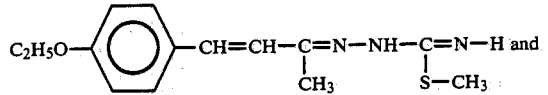 and
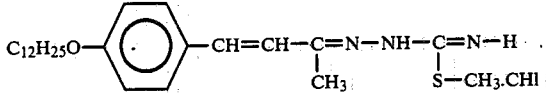
* * * * *